(12) United States Patent
Forsell

(10) Patent No.: US 6,915,165 B2
(45) Date of Patent: Jul. 5, 2005

(54) INTESTINE DYSFUNCTION TREATMENT APPARATUS

(75) Inventor: Peter Forsell, Menzingen (CH)

(73) Assignee: Obtech Medical AG, Zugerstrasse (CH)

( * ) Notice: Subject to any disclaimer, the term of this patent is extended or adjusted under 35 U.S.C. 154(b) by 143 days.

(21) Appl. No.: 09/893,510

(22) Filed: Jun. 29, 2001

(65) Prior Publication Data

US 2003/0009221 A1 Jan. 9, 2003

(30) Foreign Application Priority Data

Jun. 28, 2001 (SE) .............................................. 0102313

(51) Int. Cl.$^7$ ................................................ A61N 1/18
(52) U.S. Cl. ............................. 607/40; 607/39; 607/41; 607/62; 600/30; 606/197
(58) Field of Search ............................. 623/14, 13, 24, 623/25, 23.65; 606/197; 600/30; 602/67; 607/39, 40, 41, 62

(56) References Cited

U.S. PATENT DOCUMENTS

| | | | |
|---|---|---|---|
| 3,810,259 A | * 5/1974 | Summers | ..................... 600/30 |
| 4,222,377 A | 9/1980 | Burton | |
| 4,739,764 A | * 4/1988 | Lue et al. | ..................... 607/40 |
| 5,593,443 A | 1/1997 | Carter et al. | |
| 5,782,745 A | * 7/1998 | Benderev | ..................... 600/30 |
| 5,978,712 A | * 11/1999 | Suda et al. | ..................... 607/41 |
| 6,135,945 A | * 10/2000 | Sultan | ..................... 600/30 |
| 6,223,083 B1 | * 4/2001 | Rosar | ..................... 607/60 |
| 6,238,423 B1 | * 5/2001 | Bardy | ..................... 607/40 |
| 6,537,200 B2 | * 3/2003 | Leysieffer et al. | ............ 600/25 |

* cited by examiner

*Primary Examiner*—Corrine McDermott
*Assistant Examiner*—Kamrin Landrem
(74) *Attorney, Agent, or Firm*—Nixon & Vanderhye P.C.

(57) ABSTRACT

An intestine dysfunction treatment apparatus comprises an electric stimulation device (56) implanted in a patient, who suffers from intestine dysfunction. The stimulation device comprises electric conductors adapted to directly engage with a muscle that directly or indirectly affects the transportation of the content of the patient's intestines, for example the anal sphincter (58) or a portion of the muscle that contracts the bowels, to electrically stimulate the muscle to increase the tonus thereof. A control device (62) is provided for controlling a source of energy (64), which may or may not be implanted, to release electric energy for use in connection with the power of the stimulation device. The apparatus can be used for treating patients suffering from anal incontinence or constipation.

64 Claims, 4 Drawing Sheets

INTESTINE DYSFUNCTION TREATMENT APPARATUS

The present invention relates to an intestine dysfunction treatment apparatus, comprising an electric stimulation device implantable in a patient, who suffers from intestine dysfunction. (The term "patient" includes an animal or a human being.)

Intestine dysfunction may involve disability of controlling the muscle that contracts the bowels, colon or rectum to provide transportation of the content thereof. Such a disability usually causes constipation. In particular paralysed patients may suffer from constipation. Furthermore, intestine dysfunction may involve anal incontinence, i.e disability to close the anal sphincter.

Anal incontinence is a widespread disease. Several kinds of sphincter plastic surgery are used today to remedy anal incontinence. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later. Another disadvantage is that the use of hydraulic fluid always entails a risk of fluid leaking from the implanted hydraulic system.

Furthermore, it is a rather complicated task to manually pump the reservoir when defecation is needed. U.S. Pat. No. 5,593,443 discloses hydraulic anal sphincter under both reflex and voluntary control. An inflatable artificial sphincter with the pump system in scrotum is disclosed in U.S. Pat. No. 4,222,377.

U.S. Pat. No. 4,739,764 discloses a method for treating anal incontinence by electric stimulation of nerves connected to muscles controlling the anal sphincter. The function of the anal sphincter is affected by applying electric pulse trains on the nerves.

The object of the present invention is to provide a new convenient intestine dysfunction treatment apparatus, the performance of which may be affected by the patient at any time after operation, in particular when various needs arise over the course of a day, so that the patient substantially always is satisfied or comfortable.

This object is achieved by an intestine treatment apparatus of the kind stated initially characterised in that the stimulation device comprises electric conductors adapted to directly engage with a muscle that directly or indirectly affects the transportation of the content of the patient's intestines, to electrically stimulate the muscle to increase the tonus thereof.

As opposed to the prior art solution according to the above-noted U.S. Pat. No. 4,739,764, which requires complicated surgery to identify the relevant nerve or nerves and application of electrodes thereto, the apparatus of the present invention is easy and foolproof to implant. Accordingly, the surgeon can easily engage the electric conductors with the muscle in question without need for identifying specific nerves.

Muscles that directly affect the transportation of the content of the patient's intestines include the anal sphincter and muscles that are capable of contracting the intestines, i.e. the wall muscle of the intestines. A muscle that indirectly affects the transportation of the content of the patient's intestines may be the rectus abdominis of a patient who has iliostomy, jejunostomy, colostomy or rectostomy. For example, in a colostomy patient a portion of the colon is pulled through the rectus abdominis, which means that when stimulated the rectus abdominis can function as an anal sphincter. Any of these muscles may be selected for engagement with the stimulation device of the invention.

The apparatus preferably comprises a source of energy and a control device controllable from outside the patient's body for controlling the source of energy to release energy for use in connection with the power of the stimulation device, when the stimulation device is implanted. As a result, the apparatus of the invention provides a simple and effective control of the energy supplied to implanted components of the apparatus which ensures an extended and reliable functionality of the apparatus, possibly for the rest of the patient's life and at least many years.

An important problem is that the voltage intensity strong enough to provide the desired stimulation of the anal sphincter might fade over time, due to increasing electric resistance caused by the formation of fibrosis where the conductors engage the anal sphincter. This problem is solved by a main embodiment of the present invention, in which the electric source of energy provides a current through the electric conductors. More particularly, the control device is adapted to control the electric source of energy to release electric energy such that the intensity of the current through the electric conductors amounts to a predetermined value. As a result, decreasing current intensity caused by the formation of fibrosis where the conductors engage the anal sphincter can be compensated for. Thus, if the current through the conductors decreases the control device automatically controls the electric source of energy to release more electric energy to restore the desired current intensity.

Advantageously, the control device is adapted to control the electric source of energy to release energy in the form of an alternating current. The inventor has found that unlike an alternating current a direct current could cause electrolysis in the muscle. Such electrolysis could injure the muscle.

The control device may also control the stimulation device.

Where the selected muscle comprises the anal sphincter, the patient is enabled to keep the anal sphincter completely closed by means of the stimulation device by using the control device whenever he likes during the day. Normally, the stimulation device is always powered except when the patient wants to defecate.

In accordance with a preferred embodiment of the invention, the source of energy comprises an electric source of energy and the control device is adapted to supply the stimulation device with electric energy from the electric source of energy. In the preferred embodiment, the control device is adapted to control the stimulation device to vary the intensity of the electric stimulation of the selected muscle over time. Preferably, the control device is controllable from outside the patient's body to control the stimulation device to change the intensity of the electric stimulation of the muscle so that the muscle tonus is changed.

Where the selected muscle comprises the anal sphincter, the control device is adapted to continuously supply the stimulation device with electric energy from the electric source of energy to keep the anal sphincter closed, except when the patient wants to defecate. The control device may be controllable by the patient to control the stimulation device to increase the intensity of the electric stimulation of the anal sphincter so that the tonus of the anal sphincter is increased, when the patient feels rectum contractions. Furthermore, the control device may be controllable by the patient to control the stimulation device to cease supplying the stimulation device with electric energy when the patient wants to defecate, and to decrease the intensity of the electric stimulation of the anal sphincter so that the tonus of the anal sphincter is decreased, when the patient wants to release gas from the rectum.

Where the selected muscle comprises the rectus abdominis of a patient who has iliostomy, jejunostomy, colostomy or rectostomy, the control device may be adapted to continuously supply the stimulation device with electric energy from the electric source of energy to stimulate the rectus abdominis, except when the patient wants to defecate.

Where the selected muscle comprises the wall muscle of the intestines of a patient who has iliostomy, jejunostomy, colostomy or rectostomy, the control device may be adapted to continuously supply the stimulation device with electric energy from the electric source of energy to stimulate the wall muscle of the intestines to close the intestines, except when the patient wants to defecate.

Where the selected muscle is capable of contracting the patient's large bowel in a wave-like manner for transporting the faeces therein, the control device is adapted to control the electric source of energy to momentarily supply the stimulation device with electric energy to cause the muscle to momentarily contract the bowel in said wave-like manner. Advantageously, the control device is controllable by the patient to power the stimulation device to cause the muscle to contract the large bowel in said wave-like manner, in order to avoid constipation.

All of the embodiments of the present invention may be combined with at least one implantable sensor for sensing at least one physical parameter of the patient. Where the selected muscle comprises the anal sphincter the sensor may be adapted to sense as the physical parameter the pressure against the anal sphincter exerted by the faecal passageway. To make sure that the anal sphincter is safely closed when the patient's rectum is contracted, the electric stimulation device suitably is adapted to increase the stimulation intensity on the anal sphincter in response to the sensor sensing an abrupt increase in pressure caused by rectum contraction. As a result, the anal sphincter is kept firmly closed so that involuntary rectum contraction will not give rise to incontinence. Alternatively, the sensor may be adapted to sense as the physical parameter the patient's orientation, and the electric stimulation device may be adapted to decrease the stimulation intensity on the anal sphincter in response to the sensor sensing that the patient is lying.

The sensor may comprise a pressure sensor for directly or indirectly sensing the pressure in the faecal passageway. The expression "indirectly sensing the pressure in the faecal passageway" should be understood to encompass the cases where the sensor senses the pressure against the stimulation device or human tissue of the patient.

The control device may comprise an internal control unit to be implanted in the patient. The internal control unit may suitably directly control the stimulation device in response to signals from the sensor. In response to signals from the sensor, for example pressure, the patient's position, faecal passageway contraction or any other important physical parameter, the internal control unit may send information thereon to outside the patient's body. The internal control unit may also automatically control the stimulation device in response to signals from the sensor. For example, where the selected muscle is the anal sphincter, depending on the different needs of the individual patients the internal control unit may control the stimulation device either to efficiently stimulate the anal sphincter, so that the anal sphincter for certain is completely closed, or to reduce the stimulation, in response to the sensor sensing that the patient is lying.

The control device may also, or alternatively, comprise an external control unit outside the patient's body. The external control unit may, suitably directly, control the stimulation device in response to signals from the sensor. The external control unit may store information on the physical parameter sensed by the sensor and may be manually operated to control the stimulation device based on the stored information. In addition, there may be at least one implantable sender for sending information on the physical parameter sensed by the sensor.

Where the control device comprises an internal control unit, preferably including a microprocessor, and an external control unit outside the patient's body, the internal control unit may be programmable by the external control unit, for example for controlling the stimulation device over time. Alternatively, the internal control unit may control the stimulation device over time in accordance with an activity schedule program, which may be adapted to the patient's needs.

Conveniently, the external control unit may load the internal control unit with data in accordance with a loading mode only authorised for a doctor. For specialised controls of the stimulation device, such as electric power, electric pulse frequency etc, the external control unit may control the internal control unit in accordance with a doctor mode only authorised for the doctor. For simple controls of the stimulation device, such as on and off, the external control unit may control the internal control unit in accordance with a patient mode permitted for the patient. Thus, by using the external control unit in accordance with different modes it is possible to have certain functions of the stimulation device controlled by the patient and other more advanced functions controlled by the doctor, which enables a flexible post-operation treatment of the patient.

The control device may be adapted to control the source of energy to release energy, for instance to intermittently release energy in the form of a train of energy pulses, for direct use in connection with the power of the stimulation device. In accordance with a suitable embodiment the control device controls the source of energy to release electric energy, and the apparatus further comprises an implantable capacitor for producing the train of energy pulses from the released energy. In this case the term "direct" is used to mean, on one hand, that the released energy is used while it is being released by the control device, on the other hand, that the released energy may be somewhat delayed, in the order of seconds, by for instance an energy stabiliser before being used in connection with the power of the stimulation device.

In accordance with an embodiment of the invention, the apparatus comprises implantable electrical components including at least one, or only one single voltage level guard and a capacitor or accumulator, wherein the charge and discharge of the capacitor or accumulator is controlled by use of the voltage level guard.

In accordance with a first main aspect of the invention, the source of energy is external to the patient's body and the control device controls the source of energy to release wireless energy. An additional source of energy may be implanted in the patient, wherein the implanted source of energy is activated by wireless energy released from the external source of energy, to supply energy, which is used in connection with the power of the stimulation device.

Alternatively, an energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy. Where the control device comprises an implantable control unit the electronic circuit thereof and the stimulation device may be directly powered with transformed wireless energy, or energy from either the implanted energy storage device or battery.

In accordance with a second main aspect of the invention, the wireless energy is directly used for the power of the stimulation device, i.e. the stimulation device is powered as the wireless energy is released from the external source of energy by the control device. In this case the term "directly" is used to mean, on one hand, that the stimulation device is promptly powered by using the released energy whiteout first storing the latter, on the other hand, that the released energy may be somewhat delayed, in the order of seconds, by for instance an energy stabiliser before being used for the power of the stimulation device. As a result, a very simple control of the stimulation device is achieved and there are only a few implanted components of the apparatus. For example, there is no implanted source of energy, such as a battery, nor any implanted complicated signal control system. This gives the advantage that the apparatus will be extremely reliable.

In accordance with a third main aspect of the invention, the source of energy comprises an implantable internal source of energy. Thus, when the internal source of energy is implanted in a patient the control device controls it from outside the patient's body to release energy. This solution is advantageous for sophisticated embodiments of the apparatus that have a relatively high consumption of energy that cannot be satisfied by direct supply of wireless energy.

The internal source of energy preferably comprises an electric source of energy, such as an accumulator or a battery.

In accordance with a fourth main aspect of the invention, the apparatus comprises a switch implanted in the patient for directly or indirectly switching the power of the stimulation device and an internal electric source of energy, such as a battery, implanted in the patient for supplying electric energy for the power of the stimulation device, wherein the switch directly or indirectly affects the supply of electric energy from the internal electric source of energy. This solution is advantageous for embodiments of the apparatus that have a relatively high consumption of energy that cannot be met by direct supply of wireless energy.

In a first particular embodiment in accordance with the fourth main aspect of the invention, the switch switches between an off mode, in which the internal electric source of energy is not in use, and an on mode, in which the internal electric source of energy supplies electric energy for the power of the stimulation device. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted electric source of energy, such as a battery, can be significantly prolonged, since the implanted source of energy does not supply energy when the switch is in its off mode.

In a second particular embodiment in accordance with the fourth main aspect of the invention, the control device comprises a wireless remote control for controlling the internal electric source of energy. In this case, the switch is operable by the wireless energy from the external source of energy to switch between an off mode, in which the internal electric source of energy and remote control are not in use, and a standby mode, in which the remote control is permitted to control the internal electric source of energy to supply electric energy for the power of the stimulation device.

In a third particular embodiment in accordance with the fourth main aspect of the invention, the apparatus further comprises an energy transforming device to be implanted in the patient for transforming the wireless energy into storable energy, and an implantable energy storage device for storing the storable energy, wherein the switch is operable by energy from the implanted energy storage device to switch between an off mode, in which the internal electric source of energy is not in use, and an on mode, in which the internal electric source of energy supplies electric energy for the power of the stimulation device. In this case, the control device suitably comprises a wireless remote control for controlling the energy storage device to operate the switch.

An external data communicator may be provided outside the patient's body and an internal data communicator to be implanted in the patient may be provided for communicating with the external data communicator. The internal data communicator may feed data related to the patient, or related to the stimulation device, back to the external data communicator. Alternatively or in combination, the external data communicator may feed data to the internal data communicator. The internal data communicator may suitably feed data related to at least one physical signal of the patient.

Suitably, an implantable stabiliser, such as a capacitor, a rechargeable accumulator or the like, may be provided for stabilising the electric energy released by the control device. In addition, the control device may control the source of energy to release energy for a determined time period or in a determined number of energy pulses.

All of the above embodiments are preferably remote controlled. Thus, the control device advantageously comprises a wireless remote control transmitting at least one wireless control signal for controlling the stimulation device. With such a remote control it will be possible to adapt the function of the apparatus to the patient's need in a daily basis, which is beneficial with respect to the treatment of the patient.

The wireless remote control may be capable of obtaining information on the condition of the stimulation device and of controlling the stimulation device in response to the information. Also, The remote control may be capable of sending information related to the stimulation device from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable in the patient.

The remote control may transmit a carrier signal for carrying the control signal, wherein the carrier signal is frequency, amplitude or frequency and amplitude modulated and is digital, analogue or digital and analogue. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analogue, and may comprise an electric or magnetic field. Suitably, the wireless remote control may transmit an electromagnetic carrier wave signal for carrying the digital or analogue control signal. For example, use of an analogue carrier wave signal carrying a digital control signal would give safe communication. The control signal may be transmitted in pulses by the wireless remote control.

The control device may be activated in a manual or non-manual manner to control the source of energy to release energy.

In the above-presented embodiments of the invention the released energy may comprise electric energy and an implantable capacitor having a capacity less than 0, 1 $\mu$F may be provided for producing the above-mentioned train of energy pulses.

Generally, the wireless energy comprises a signal.

The apparatus may further comprise an implantable energy transforming device for transforming wireless energy, for example in the form of sound waves, directly or indirectly into electric energy, for the power of the stimulation device. More specifically, the energy transforming device may comprise a capacitor adapted to produce electric pulses from the transformed electric energy.

Generally, the stimulation device advantageously is embedded in a soft or gel-like material, such as a silicone material having hardness less than 20 Shore.

The electric conductors may comprise hooks to secure the electric conductors on the muscle.

Where the selected muscle comprises the anal sphincter or extends around a portion of the bowels or rectus abdominis, the stimulation device suitably comprises a band for application around the anal sphincter or the portion of the bowels or rectus abdominis, wherein the band is provided with the electric conductors for engaging the muscle. In this case, the electric conductors may also comprise the above-mentioned hooks.

All the above described various components may be combined in the different embodiments where applicable. Also the various functions described in connection with the above embodiments of the invention may be used in different applications, where applicable.

All the various ways of transferring energy and controlling the energy presented in the present specification may be practised by using all of the various components and solutions described.

The present invention also provides methods for treating intestine dysfunction.

Accordingly, in accordance with a first alternative method, there is provided a method of treating intestine dysfunction, comprising the steps of implanting an electric stimulation device in a patient, so that the stimulation device engages a muscle that directly or indirectly affects the transportation of the content of the patient's intestines, providing an electric source of energy, and controlling the electric source of energy to power the stimulation device to electrically stimulate the muscle to increase the tonus thereof.

The first alternative method may also be performed laparascopically. Thus, there may be provided a laparascopic method of treating intestine dysfunction, comprising the steps of laparascopically implanting an electric stimulation device in a patient, so that the stimulation device engages a muscle that directly or indirectly affects the transportation of the content of the patient's intestines, providing an electric source of energy, and controlling the electric source of energy to power the stimulation device to electrically stimulate the muscle to increase the tonus thereof.

In accordance with a second alternative method, there is provided a method of treating a patient suffering from intestine dysfunction, comprising: (a) Surgically implanting in the patient an electric stimulation device engaging a muscle that directly or indirectly affects the transportation of the content of the patient's intestines. (b) Providing a source of energy external to the patient's body. (c) Controlling the external source of energy from outside the patient's body to release wireless energy. And (d) using the released wireless energy in connection with the powering of the stimulation device.

The second alternative method may further comprise implanting an energy transforming device, controlling the external source of energy to release wireless energy, and transforming the wireless energy by the energy transforming device into energy different from the wireless energy for use in connection with the power of the stimulation device. This method may further comprise implanting a stabiliser in the patient for stabilising the energy transformed by the energy transforming device.

The invention is described in more detail in the following with reference to the accompanying drawings, in which FIG. 1 is a schematic block diagram illustrating an embodiment of the intestine dysfunction treatment apparatus of the invention, in which wireless energy is released from an external source of energy for use in the power of a stimulation device;

Referring to the drawing figures, like reference numerals designate identical or corresponding elements throughout the several figures.

Figure 1:
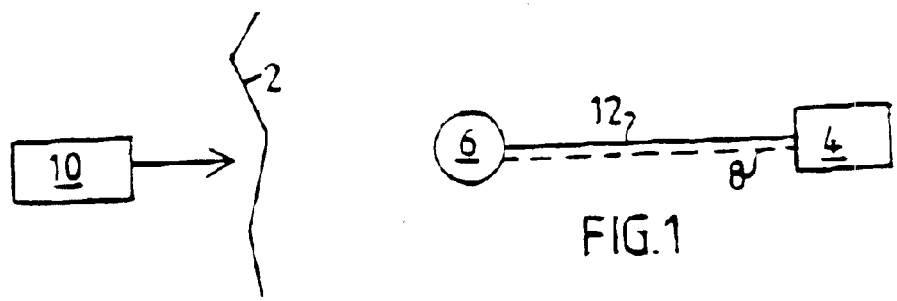

FIG. 1 schematically shows an embodiment of the intestine dysfunction treatment apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body. The apparatus of FIG. 1 comprises an implanted electric stimulation device 4, which engages the muscle tissue of the patient's anal sphincter by means of electric conductors. An implanted control unit 6 controls the stimulation device 4 via a control line 8. An external control unit 10 includes an external source of energy and a wireless remote control transmitting a control signal generated by the external source of energy. The control signal is received by a signal receiver incorporated in the implanted control unit 6, whereby the control unit 6 controls the implanted stimulation device 4 in response to the control signal. The implanted control unit 6 also uses electric energy drawn from the control signal for powering the stimulation device 4 via a power supply line 12.

Figure 2:
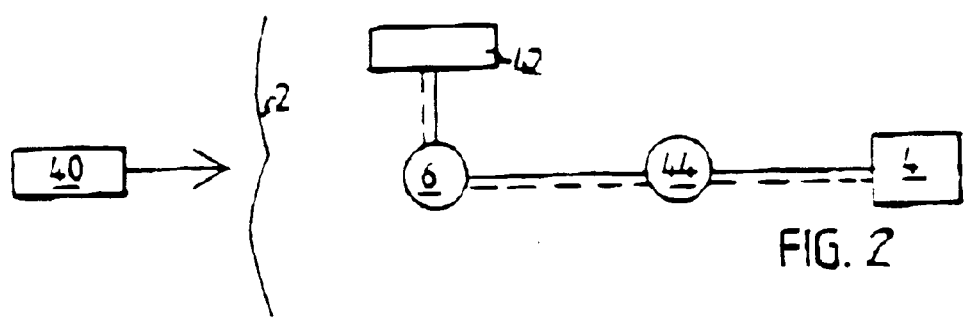
FIG. 2 is a schematic block diagram illustrating another embodiment of the invention, in which wireless energy is released from an internal source of energy.

FIG. 2 shows an embodiment of the invention identical to that of FIG. 1, except that an implanted internal electric source of energy in the form of a battery 42 is substituted for the external source of energy. Thus, an external control unit 40 without any source of energy is used in this embodiment. In response to a control signal from the external control unit 40 the implanted control unit 6 powers the stimulation device 4 with energy from the battery 42.

Figure 3:
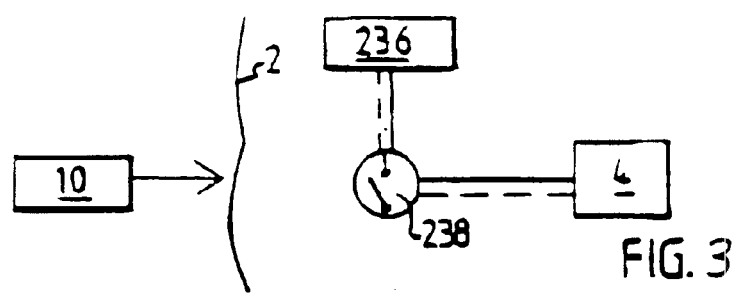
FIGS. 3 to 6 are schematic block diagrams illustrating four embodiments, respectively, of the invention, in which a switch is implanted in the patient for directly or indirectly switching the power of the stimulation device.

FIG. 3 shows an embodiment of the invention comprising the stimulation device 4, the external control unit 10, and an implanted source of energy 236 and an implanted switch 238. The switch 238 is operated by wireless energy released from the external source of energy of the external control unit 6 to switch between an off mode, in which the implanted source of energy 236 is not in use, and an on mode, in which the implanted source of energy 236 supplies energy for the power of the stimulation device 4.

Figure 4:
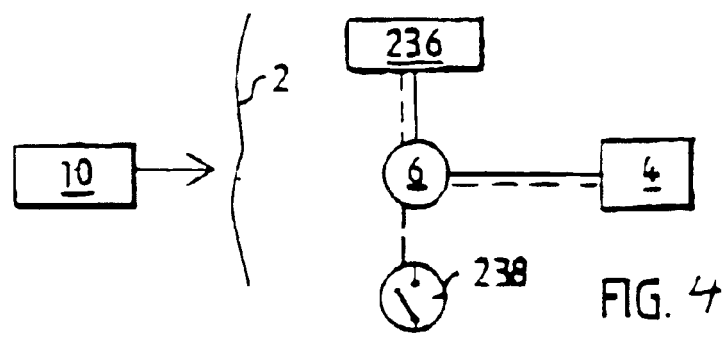

FIG. 4 shows an embodiment of the invention identical to that of FIG. 3, except that also the control unit 6 is implanted, in order to receive a control signal from the wireless remote control of the external control unit 10. The switch 238 is operated by the wireless energy from the external source of energy 10 to switch between an off mode, in which the implanted source of energy 236 and the wireless remote control of the external control unit 10 are not in use, i.e. the control unit 6 is not capable of receiving the control signal, and a standby mode, in which the wireless remote control is permitted to control the internal source of energy 236, via the implanted control unit 6, to supply energy for the power of the stimulation device 4.

Figure 5:
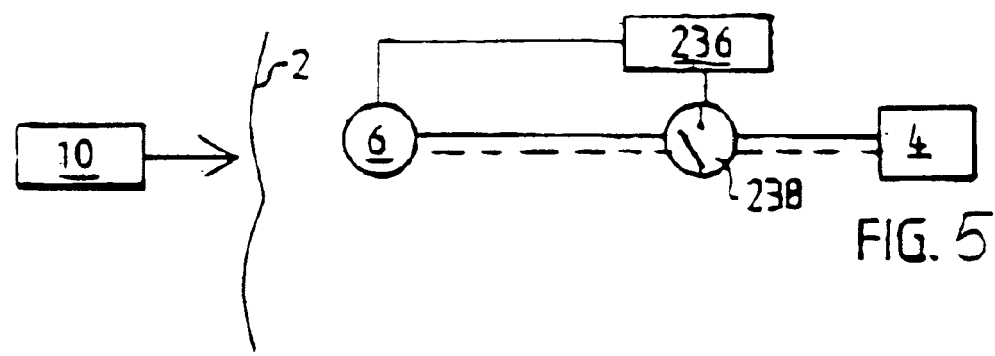

FIG. 5 shows an embodiment of the invention identical to that of FIG. 4, except that an energy transforming device for transforming the wireless energy into storable energy is incorporated in the implanted control unit 6 and that the implanted source of energy 236 is of a type that is capable of storing the storable energy. In this case, in response to a control signal from the external control unit 10, the implanted control unit 6 controls the switch 238 to switch from an off mode, in which the implanted source of energy 236 is not in use, to an on mode, in which the source of energy 236 supplies energy for the power of the stimulation device 4.

Figure 6:
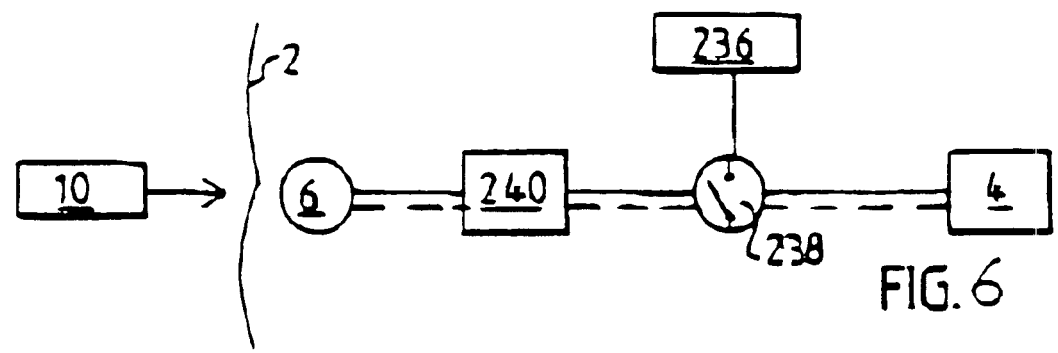

FIG. 6 shows an embodiment of the invention identical to that of FIG. 5, except that an energy storage device 240 also is implanted in the patient for storing the storable energy transformed from the wireless energy by the transforming device of the control unit 6. In this case, the implanted control unit 6 controls the energy storage device 240 to operate the switch 238 to switch between an off mode, in which the implanted source of energy 236 is not in use, and an on mode, in which the implanted source of energy 236 supplies energy for the power of the stimulation device 4.

Figure 7:
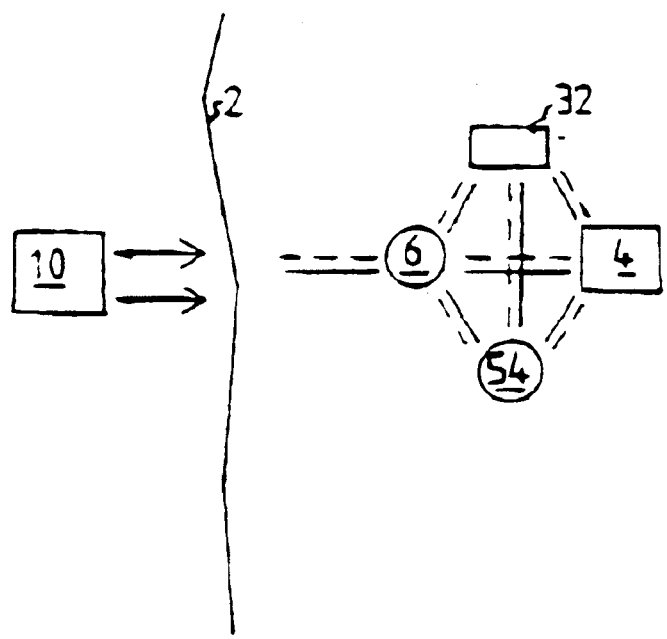
FIG. 7 is a schematic block diagram illustrating conceivable combinations of implantable components for achieving various communication options.

FIG. 7 schematically shows conceivable combinations of implanted components of the apparatus for achieving various communication possibilities. Basically, there are the implanted stimulation device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted stimulation device 4 in response to the control signal.

A sensor 54 may be implanted in the patient for sensing a physical parameter of the patient, such as the pressure in the faecal passageway. The control unit 6, or alternatively the external control unit 10, may control the stimulation device 4 in response to signals from the sensor 54. A transceiver may be combined with the sensor 54 for sending information on the sensed physical parameter to the external control unit 10. The wireless remote control of the external control unit 10 may comprise a signal transmitter or transceiver and the implanted control unit 6 may comprise a signal receiver or transceiver. Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the stimulation device from inside the patient's body to the outside thereof. For example, the battery 32 may be equipped with a transceiver for sending information on the charge condition of the battery.

Those skilled in the art will realise that the above various embodiments according to FIGS. 1–6 could be combined in many different ways.

Figure 8:
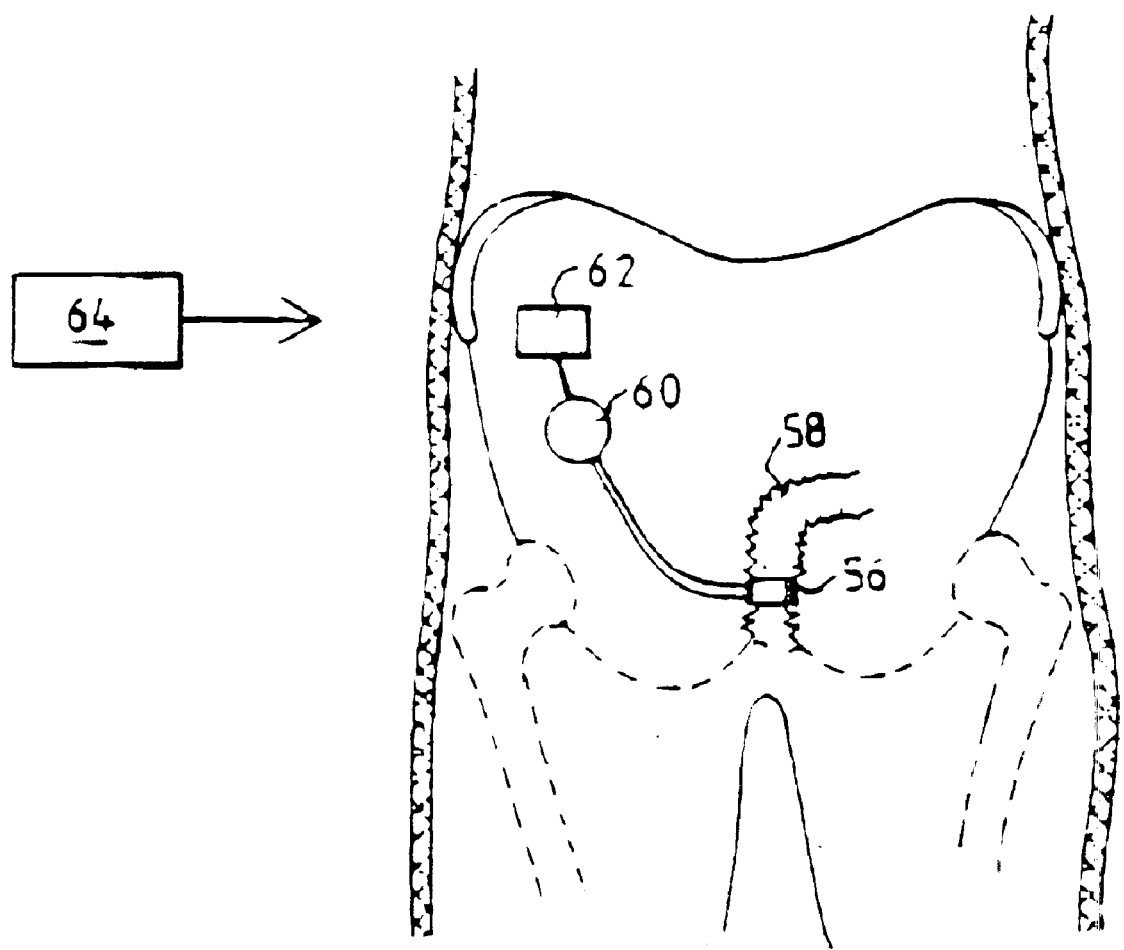
FIG. 8 illustrates the apparatus in accordance with the invention implanted in a patient.

FIG. 8 illustrates how any of the above-described embodiments of the anal incontinence treatment apparatus of the invention may be implanted in a patient. Thus, an assembly of the apparatus implanted in the patient comprises a stimulation device in the form of a band 56, which is wrapped around the anal sphincter 58. The band 58 is provided with conductors that engage the muscle tissue of the anal sphincter, so that an electric connection is established between the conductors and the muscle tissue. An implanted control unit 60 is provided for controlling the supply of electric energy to the band 56. There is an implanted energy transforming device 62 for transforming wireless energy into electric energy. The transforming device 62 also includes a signal receiver. An external control unit 64 includes a signal transmitter for transmitting a control signal to the signal receiver of the implanted transforming device 62. The transforming device 62 is capable of transforming signal energy from the control signal into electric energy for powering the stimulation device 56 and for energising other energy consuming implanted components of the apparatus.

Figure 9:
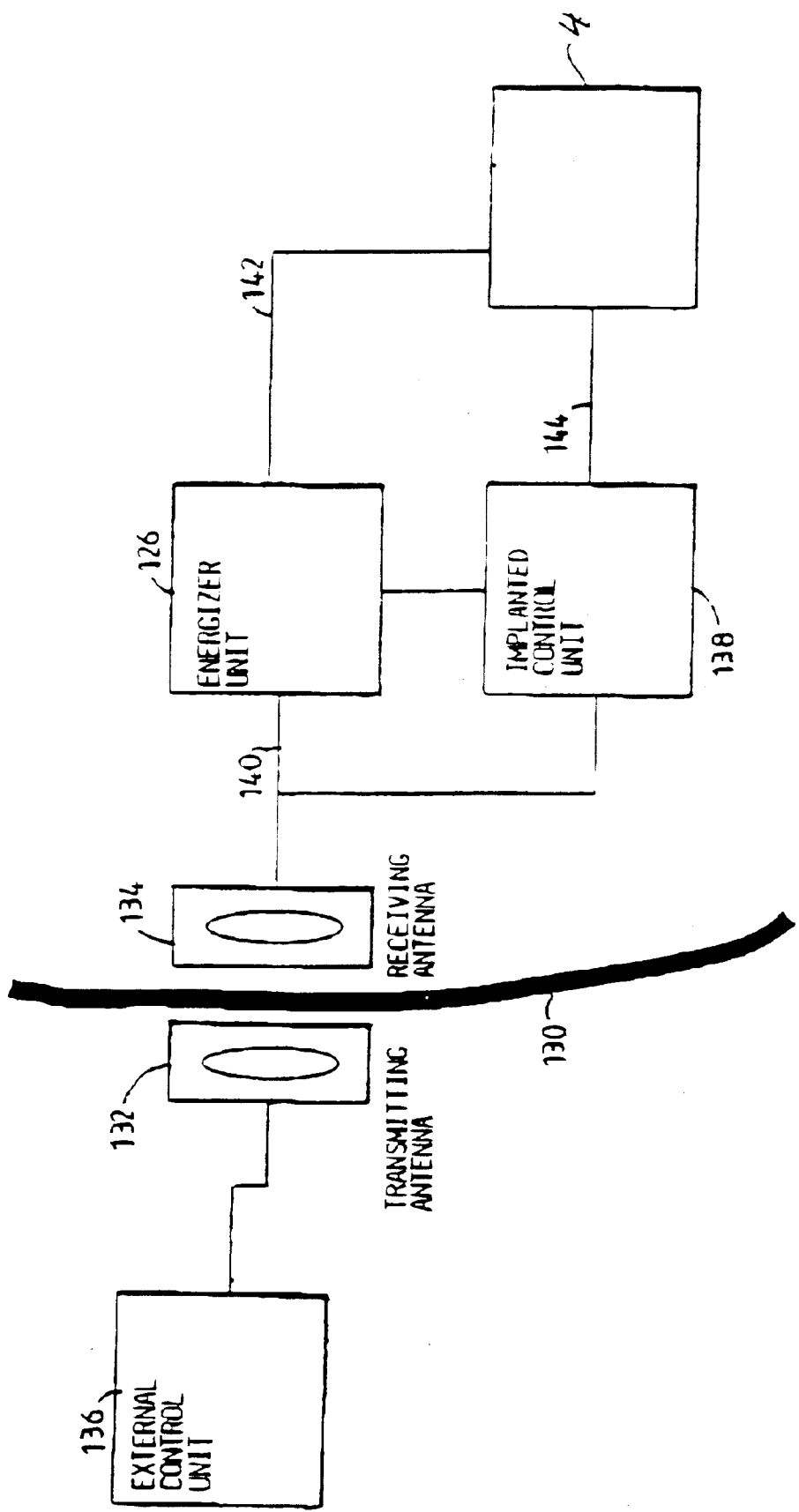
FIG. 9 is a block diagram illustrating remote control components of an embodiment of the invention.

FIG. 9 shows the basic parts of a wireless remote control of the apparatus of the invention including an implanted electric stimulation device 4. In this case, the remote control is based on the transmission of electromagnetic wave signals, often of high frequencies in the order of 100 kHz–1 gHz, through the skin 130 of the patient. In FIG. 9, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132, 134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either power or not power the stimulation device. The microprocessor starts a command by applying a high frequency signal on the antenna 132. After a short time, when the signal has energised the implanted parts of the control system, commands are sent to power the stimulation device. The commands are sent as digital packets in the form illustrated below.

| Start pattern, | Command, | Count, | Checksum, |
|---|---|---|---|
| 8 bits | 8 bits | 8 bits | 8 bits |

The commands may be sent continuously during a rather long time period. When a new power or non-power step is desired the Count byte is increased by one to allow the implanted control unit 138 to decode and understand that another step is demanded by the external control unit 136. If any part of the digital packet is erroneous, its content is simply ignored.

Through a line 140, an implanted energiser unit 126 draws energy from the high frequency electromagnetic wave signals received by the receiving antenna 134. The energiser unit 126 stores the energy in a power supply, such as a large capacitor, powers the control unit 138 and powers the electric stimulation device 4 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energiser unit 126 has sufficient energy stored, powers the stimulation device 4 via a line 144.

Alternatively, the energy stored in the power supply of the energiser unit may only be used for powering a switch, and the energy for powering the stimulation device 4 may be obtained from another implanted power source of relatively high capacity, for example a battery. In this case the switch is adapted to connect said battery to the control unit 138 in an on mode when the switch is powered by the power supply and to keep the battery disconnected from the control unit in a standby mode when the switch is not powered.

What is claimed is:

1. An intestine dysfunction treatment apparatus, comprising:
    an electric stimulation device implantable in a patient, who suffers from intestine dysfunction,
    electric conductors of the electric stimulation device adapted to directly engage with a muscle that directly or indirectly affects the transportation of the content of the patient's intestines, to electrically stimulate the muscle to increase the tonus thereof,
    an internal electric source of energy implantable in the patient, and
    a control device controllable from outside the patient's body to control the internal electric source of energy to release electric energy for use in connection with the power of the stimulation device, when the stimulation device is implanted, the electric energy being in the form of an alternating current through the electric conductors, the intensity of the current through the electric conductors amounting to a predetermined value,
    the control device automatically controlling the electric source of energy to release more electric energy to restore the predetermined value of current intensity when the current through the conductors decreases.

2. An apparatus according to claim 1, wherein the control device controls the stimulation device.

3. An apparatus according to claim 2, wherein the control device controls the stimulation device to vary the intensity of the electric stimulation of the muscle over time.

4. An apparatus according to claim 3, wherein the control device is controllable from outside the patient's body to control the stimulation device to change the intensity of the electric stimulation of the muscle so that the muscle tonus is changed.

5. An apparatus according to claim 4, wherein the muscle comprises the anal sphincter, and the control device continuously supplies the stimulation device with electric energy from the electric source of energy to keep the anal sphincter closed, except when the patient wants to defecate.

6. An apparatus according to claim 5, wherein the control device is controllable by the patient to control the stimulation device to increase the intensity of the electric stimulation of the anal sphincter so that the tonus of the anal sphincter is increased, when the patient feels rectum contractions.

7. An apparatus according to claim 5, wherein the control device is controllable by the patient to control the stimulation device to cease supplying the stimulation device with electric energy when the patient wants to defecate.

8. An apparatus according to claim 5, wherein the control device is controllable by the patient to control the stimulation device to decrease the intensity of the electric stimulation of the anal sphincter so that the tonus of the anal sphincter is decreased, when the patient wants to release gas from the rectum.

9. An apparatus according to claim 2, wherein the muscle is capable of contracting the patient's large bowel in a wave-like manner for transporting the feces therein, and the control device controls the electric source of energy to momentarily supply the stimulation device with electric energy to cause the muscle to momentarily contract the bowel in said wave-like manner.

10. An apparatus according to claim 9, wherein the control device is controllable by the patient to power the stimulation device to cause the muscle to contract the large bowel in said wave-like manner, in order to avoid constipation.

11. An apparatus according to claim 2, wherein the control device comprises an internal control unit implantable in the patient for controlling the stimulation device.

12. An apparatus according to claim 11, wherein the internal control unit is programmable.

13. An apparatus according to claim 12, wherein the control device comprises an external control unit intended to be outside the patient's body, the internal control unit being programmable by the external control unit.

14. An apparatus according to claim 13, wherein the external control unit loads the internal control unit with data in accordance with a loading mode only authorised for a doctor.

15. An apparatus according to claim 13, wherein the external control unit controls the internal control unit in accordance with a doctor mode only authorised for a doctor.

16. An apparatus according to claim 13, wherein the external control unit controls the internal control unit in accordance with a patient mode permitted for the patient.

17. An apparatus according to claim 12, wherein the internal control unit is programmable for controlling the stimulation device over time.

18. An apparatus according to claim 17, wherein the internal control unit controls the stimulation device over time in accordance with an activity schedule program.

19. An apparatus according to claim 17, wherein the internal control unit comprises a microprocessor.

20. An apparatus according to claim 2, wherein the muscle comprises the rectus abdominis of the patient who has iliostomy, jejunostomy, colostomy or rectostomy therethrough, and the control device is adapted to continuously supply the stimulation device with electric energy from the electric source of energy to stimulate the rectus abdominis to close the patient's intestines, except when the patient wants to defecate.

21. An apparatus according to claim 2, wherein the muscle comprises the wall muscle of the intestines of the patient who has iliostomy, jejunostomy, colostomy or rectostomy, and the control device is adapted to continuously supply the stimulation device with electric energy from the electric source of energy to stimulate the wall muscle of the intestines to close the intestines, except when the patient wants to defecate.

22. An apparatus according to claim 1, further comprising at least one implantable sensor for sensing at least one physical parameter of the patient.

23. An apparatus according to claim 22, wherein the muscle comprises the anal sphincter and the sensor senses as the physical parameter the pressure against the anal sphincter exerted by the fecal passageway.

24. An apparatus according to claim 23, wherein the electric stimulation device increases the stimulation intensity on the anal sphincter in response to the sensor sensing an abrupt increase in pressure caused by rectum contraction.

25. An apparatus according to claim 22, wherein the muscle comprises the anal sphincter and the sensor senses as the physical parameter the patient's orientation.

26. An apparatus according to claim 25, wherein the electric stimulation device decreases the stimulation intensity on the anal sphincter in response to the sensor sensing that the patient is lying down.

27. An apparatus according to claim 22, wherein the sensor comprises a pressure sensor for directly or indirectly sensing as the physical parameter the pressure in the fecal passageway of the patient.

28. An apparatus according to claim 22, wherein the control device is controls the stimulation device in response to signals from the sensor.

29. An apparatus according to claim 28, wherein the control device comprises an internal control unit implantable in the patient, the internal control unit controlling the stimulation device in response to signals from the sensor.

30. An apparatus according to claim 29, wherein the control device comprises an external control unit outside the patient's body, the external control unit controlling the stimulation device in response to signals from the sensor.

31. An apparatus according to claim 30, wherein the external control unit stores information on the physical parameter sensed by the sensor and is manually operated to control the stimulation device based on the stored information.

32. An apparatus according to claim 22, further comprising at least one implantable sender for sending information on the physical parameter sensed by the sensor.

33. An apparatus according to claim 1, wherein the source of energy comprises an implantable internal electric source of energy comprising at least one accumulator, at least one capacitor or at least one rechargeable battery, or a combination of at least one capacitor and at least one rechargeable battery.

34. An apparatus according to claim 1, further comprising a switch implantable in the patient for directly or indirectly switching the power of the stimulation device.

35. An apparatus according to claim 34, wherein the switch directly or indirectly affects the supply of electric energy from the internal electric source of energy.

36. An apparatus according to claim 35, wherein the switch switches between an "off" mode, in which the internal electric source of energy is not in use, and an "on" mode, in which the internal electric source of energy supplies electric energy to the stimulation device.

37. An apparatus according to claim 35, further comprising an energy transforming device implantable in the patient for transforming the wireless energy into electric energy, which is stored by the internal electric source of energy.

38. An apparatus according to claim 37, wherein the switch switches from an "off" mode, in which the internal electric source of energy is not in use, to an "on" mode, in which the internal source of electric energy supplies energy to the stimulation device.

39. An apparatus according to claim 38, wherein the control device controls the switch to switch between the "on" and "off" modes.

40. An apparatus according to claim 39, wherein the control device comprises a wireless remote control.

41. An apparatus according to claim 1, wherein the control device comprises a wireless remote control.

42. An apparatus according to claim 1, further comprising an external data communicator intended to be outside the patient's body, and an internal data communicator implantable in the patient for communicating with the external communicator, wherein the internal data communicator feeds data related to the patient back to the external data communicator or the external data communicator feeds data to the internal data communicator.

43. An apparatus according to claim 42, wherein the internal data communicator feeds data related to the stimulation device.

44. An apparatus according to claim 42, wherein the internal data communicator feeds data related to at least one physical signal of the patient.

45. An apparatus according to claim 1, wherein the control device comprises a wireless remote control for transmitting at least one wireless control signal for controlling the stimulation device.

46. An apparatus according to claim 45, wherein the remote control is capable of obtaining information on the condition of the stimulation device when the stimulation device is implanted and to control the stimulation device in response to the information.

47. An apparatus according to claim 45, wherein the wireless remote control comprises at least one external signal transmitter or transceiver and at least one internal signal receiver or transceiver implantable in the patient.

48. An apparatus according to claim 45, wherein the wireless remote control comprises at least one external signal receiver or transceiver and at least one internal signal transmitter or transceiver implantable in the patient.

49. An apparatus according to claim 45, wherein the remote control transmits a carrier signal for carrying the control signal.

50. An apparatus according to claim 49, wherein the carrier signal is frequency, amplitude or frequency and amplitude modulated.

51. An apparatus according to claim 49, wherein the carrier signal is digital, analogue or digital and analogue.

52. An apparatus according to claim 49, wherein the control signal used with the carrier signal is frequency, amplitude or frequency and amplitude modulated.

53. An apparatus according to claim 45, wherein the control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

54. An apparatus according to claim 45, wherein the control signal comprises an electric, magnetic or electric and magnetic field.

55. An apparatus according to claim 45, wherein the control signal is digital, analogue or digital and analogue.

56. An apparatus according to claim 55, wherein the remote control transmits an electromagnetic carrier wave signal for carrying the digital or analogue control signal.

57. An apparatus according to claim 45, wherein the control signal is transmitted in pulses by the wireless remote control.

58. An apparatus according to claim 1, wherein the stimulation device is embedded in a soft or gel-like material.

59. An apparatus according to claim 1, wherein the stimulation device is embedded in a silicone material having hardness less than 20 Shore.

60. An apparatus according to claim 1, wherein the muscle comprises the anal sphincter or extends around a portion of the bowels or rectus abdominis, the stimulation device comprises a band for application around the anal sphincter or the portion of the bowels or rectus abdominis, and the band is provided with the electric conductors for engaging the muscle.

61. An apparatus according to claim 1, wherein the electric conductors comprise hooks to secure the electric conductors on the muscle.

62. An apparatus according to claim 61, wherein the hooks are to be inserted into the muscle.

63. An intestine dysfunction treatment apparatus, comprising:

an electric stimulation device implantable in a patient, who suffers from intestine dysfunction, electric conductors of the electric stimulation device adapted to directly engage with a muscle that is capable of contracting the patient's large bowel in a wave-like manner for transporting the feces therein, to electrically stimulate the muscle to increase the tonus thereof, an electric source of energy, and a control device controllable from outside the patient's body, wherein the control device is adapted to control the stimulation device and the electric source of energy to momentarily supply the stimulation device with electric energy to cause the muscle to momentarily contract the bowel in said wave-like manners, the electric source of energy releasing the electric energy in the form of an alternating current through the electric conductors, the intensity of the current through the electric conductors amounting to a predetermined value.

the control device automatically controlling the electric source of energy to release more electric energy to restore the predetermined value of current intensity when the current through the electric conductors decreases.

64. An apparatus according to claim 63, wherein the control device is controllable by the patient to power the stimulation device to cause the muscle to contract the large bowel in said wave-like manner, in order to avoid constipation.

* * * * *

UNITED STATES PATENT AND TRADEMARK OFFICE
CERTIFICATE OF CORRECTION

PATENT NO.          : 6,915,165 B2
APPLICATION NO.     : 09/893510
DATED               : July 5, 2005
INVENTOR(S)         : Forsell Page 1 of 1

It is certified that error appears in the above-identified patent and that said Letters Patent is hereby corrected as shown below:

On the Title page, item (73) "Assignee: Obtech Medical AG, Zugerstrasse (CH)" should be deleted.

Signed and Sealed this

Twenty-fourth Day of November, 2009

David J. Kappos
*Director of the United States Patent and Trademark Office*